ous Patent [19]

United States Patent

Wick et al.

[11] Patent Number: 4,663,350
[45] Date of Patent: May 5, 1987

[54] UNSATURATED DIPHENYLAZOMETHINE DERIVATIVES, THEIR PREPARATION AND PHARMACEUTICAL COMPOSITIONS CONTAINING THEM

[75] Inventors: Alexander Wick, Saint Nom-La-Bretèche; Bernard Raizon, Vigneux, both of France

[73] Assignee: Synthelabo, Paris, France

[21] Appl. No.: 780,456

[22] Filed: Sep. 26, 1985

[30] Foreign Application Priority Data

Sep. 27, 1984 [FR] France ................................ 84 14841

[51] Int. Cl.$^4$ .................. A61K 31/235; C07C 103/26
[52] U.S. Cl. .................... 514/539; 514/567; 514/619; 560/35; 562/440; 564/167
[58] Field of Search .......................... 560/35; 562/440; 564/167; 514/539, 567, 619

[56] References Cited

U.S. PATENT DOCUMENTS 4,094,992  6/1978  Kaplan et al. ........................ 560/35

Primary Examiner—Natalie Trousof
Assistant Examiner—Bruce D. Gray
Attorney, Agent, or Firm—Wegner & Bretschneider

[57] ABSTRACT

Diphenylazomethine derivatives of formula (I)

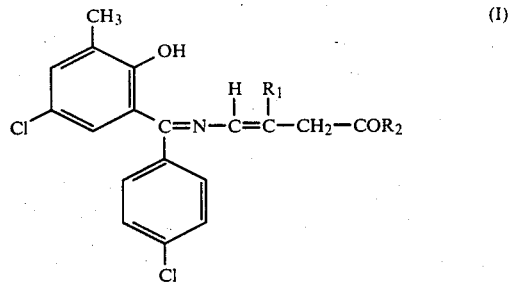

wherein $R_1$ is hydrogen or methyl and $R_2$ is an —OH, —OM (M=alkaline metal or alkaline earth metal), —NH$_2$ or —O(C$_{1-4}$ alkyl) group, and which are in the form of cis or trans isomers or mixtures thereof, have central nervous system activity and can be used as antidepressants and anticonvulsants.

3 Claims, No Drawings

UNSATURATED DIPHENYLAZOMETHINE DERIVATIVES, THEIR PREPARATION AND PHARMACEUTICAL COMPOSITIONS CONTAINING THEM

The present invention relates to diphenylazomethine derivatives having an unsaturated chain, their preparation and pharmaceutical compositions containing them.

The invention provides diphenylazomethine derivatives of formula (I)

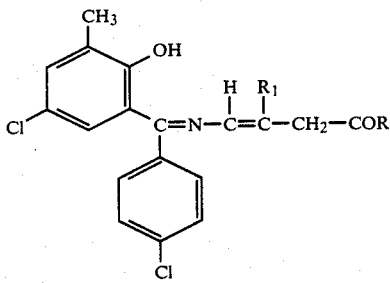

wherein $R_1$ is hydrogen or methyl and $R_2$ is an —OH, —OM (wherein M is an alkali metal or alkaline earth metal), —$NH_2$ or —$O(C_{1-4}$ alkyl) group, said derivatives being in the form of cis or trans isomers or mixtures of said isomers.

A mixture of the cis and trans isomers can be separated into the two constituent isomers by successive crystallisations.

According to the invention, the diphenylazomethine derivatives of the invention can be prepared by reacting a benzophenone of formula (II)

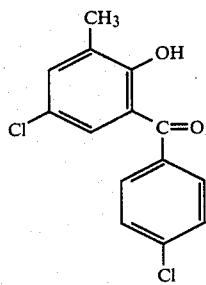

with a compound of formula (III)

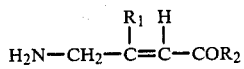

wherein $R_1$ and $R_2$ are as defined above.

The benzophenone (II) is described in French Pat. No. 81/21,559 and can be reacted with a compound (III) in a solvent such as methanol, at a temperature from 20° C. to the boiling point of the solvent.

The compounds (III) can be prepared according to conventional methods in the literature, starting from known compounds.

The compounds (I) in which $R_2$ is OM, $NH_2$ or $O(C_{1-4}$ alkyl) can be prepared from compounds (I) in which $R_2$ is OH, by conventional salification, amidification or esterification reactions.

The Examples which follow will help to illustrate the invention.

The structures of the compounds were confirmed by analyses and IR and NMR spectra.

EXAMPLE 1

4-[[(5-chloro-2-hydroxy-3-methylphenyl)(4-chlorophenyl) methylene]amino]-3-butenoic acid

1. 4-amino-2-butenoic acid

This compound is prepared from DL-4-amino-3-hydroxybutanoic acid. 15.5 g (0.13 mole) of this acid in 150 ml of concentrated (36 N) sulphuric acid are heated to 128°–130° C. for 1 h. The solution obtained is diluted in the cold with 1000 ml of water. Approximately 1200 g of $BaCO_3$ are then added until the pH is 7.5. The suspension is stirred vigorously for a long time. The precipitate formed is filtered and washed 3 times with water. The $Ba^{++}$ ions are neutralised with N sulphuric acid. The solution is filtered and concentrated to 50 ml, 150 ml of ethanol are added and the compound is left to crystallise. The acid, a mixture of both cis and trans isomers, melts at 168°–170° C. with decomposition.

2. 4-[[(5-chloro-2-hydroxy-3-methylphenyl)(4-chlorophenyl)methylene]amino]-3-butenoic acid In a 1-1 round-bottomed flask, 15.3 g (0.054 mole) of (5-chloro-2-hydroxy-3-methylphenyl)(4-chlorophenyl)-methanone, 5 g (0.049 mole) of 4-amino-2-butenoic acid and 4.5 g (0.054 mole) of sodium hydrogencarbonate are introduced in 700 ml of methanol. The mixture is evaporated to dryness on a water bath at 100° C. under reduced pressure. The operation is repeated seven times, evaporating 500 ml of methanol at a time. The dry residue is taken up with 200 ml of methylene chloride and 300 ml of water, acidified to pH 4 with 3.7 g of citric acid and then extracted with 1 of methylene chloride. The organic phase is washed with water, decanted, dried over $MgSO_4$, filtered and evaporated to dryness. The compound is crystallised in 100 ml of hexane, filtered, drained and dissolved in 100 ml of ethyl acetate. The product crystallises slowly. It is filtered, drained and washed with 10 ml of ether.

After recrystallisation, the compound, which is a mixture of both cis (45%) and trans (55%) isomers melts at 146°–7° C.

EXAMPLE 2

Transisomer of 4-[[(5-chloro-2-hydroxy-3-methylphenyl)(4-chlorophenyl)methylene]amino]-3-butenoic acid The transisomer is isolated by successive recrystallisations in ethyl acetate.

The compound melts at 202°–203° C.

EXAMPLE 3

4-[[(5-chloro-2-hydroxy-3-methylphenyl)(4-chlorophenyl)methylene]amino]-3-butenamide and its transisomer To 3.3 g of the acid obtained in Example 1, dissolved in 100 ml of tetrahydrofuran (THF), 1.6 g of carbonyldiimidazole is added and the mixture is stirred for 2 hrs. A solution is prepared of ammonia gas in 250 ml of anhydrous THF, into which the first solution obtained is introduced slowly. The mixture is stirred for 3 h and left to stand overnight. It is evaporated to dryness under reduced pressure and the residue is distributed between 150 ml of $CH_2Cl_2$ and 100 ml of water. The organic phase is decanted, dried over MgSO$_4$, filtered and evaporated to dryness. An oil is obtained which is purified by chromatography on silica (eluent: ethyl acetate). The 3 final fractions containing the products are dried over MgSO$_4$. The fractions are filtered and the filtrates evaporated to dryness. One of the 3 residues obtained, a mixture of both cis (32%) and trans (68%) isomers, is recrystallised in a mixture of ether and petroleum ether.

M.p.=170°–171° C.

The transisomer is obtained by recrystallisation of one of the residues in an ether/petroleum ether mixture. It melts at 191°–192° C.

EXAMPLE 4

Ethyl 4-[[(5-chloro-2-hydroxy-3-methylphenyl)(4-chlorophenyl)methylene]amino]-3-methyl-3-butenoate

1. Ethyl 4-amino-3-methyl-2-butenoate 1.1. To 13 g of ethyl 3-methyl-2-butenoate dissolved in 130 ml of CCl$_4$, there are added 20 g of recrystallised N-bromosuccinimide and an amount of benzoyl peroxide covering a spatula tip. The mixture is heated to refluxing temperature, while being stirred for 3 hrs. After being cooled, the precipitate is filtered and rinsed with 20 ml of CCl$_4$. The filtrate is concentrated and distilled under reduced pressure.

B.p.$_5$=75° C. n$_D^{26}$=1.4932.

1.2. A solution of 5.3 g of hexamethylenetetramine in 45 ml of CHCl$_3$ is heated while being stirred, and 7 g of the brominated compound obtained under 1.1. are added slowly. The mixture is heated to refluxing temperature while being stirred for 3 h. It is left to stand overnight. After the mixture has been cooled in an iced water bath, the precipitate is filtered, drained and dried in an oven. 5.2 g of this intermediate product, a quaternary ammonium compound, is dissolved in 10 ml of water, 50 ml of ethanol and 12 ml of concentrated hydrochloric acid. The mixture is left to stand for 24 h. It is filtered and concentrated to dryness. The residue is taken up in alcohol, the ammonium chloride precipitate filtered and the filtrate evaporated to dryness. The compound is obtained in the form of hydrochloride, an oily solid which is used as it is in the following stage.

2. Ethyl 4-[[(5-chloro-2-hydroxy-3-methylphenyl)(4-chlorophenyl)methylene]amino]-3-methyl-3-butenoate To 6 g of hydrochloride obtained under 1.2., dissolved in 150 ml of methanol, 5.6 g of sodium bicarbonate are added. The solution is evaporated to dryness under vacuum at room temperature. 400 ml of methanol and 9 g of (5-chloro-2-hydroxy-3-methylphenyl)(4-chlorophenyl)methanone are then added. The mixture is evaporated to dryness on a water bath at 80° C. The mixture is placed under vacuum. 400 ml of methanol are then successively evaporated three times under the same conditions. The residue is distributed between 200 ml of ether and 250 ml of water, and the organic phase decanted, dried over MgSO$_4$, filtered and evaporated to dryness. The compounds are separated by chromatography on silica, eluting with methylene chloride. One of the residues is recrystallised in pentane. The transisomer is obtained.

M.p.=81°–82° C.

Another residue is recrystallised in pentane, treating with vegetable charcoal. The cisisomer is obtained.

M.p.=96°–97° C.

The compounds of the invention prepared by way of examples are collated in the following table:

TABLE

Structure (I): 3-methyl-, 5-chloro-, 2-hydroxy-phenyl group connected via C=N-C(H)=C(R$_1$)-CH$_2$-COR$_2$ to 4-chlorophenyl.

| Compound | R$_1$ (CH=C—CH$_2$— with substituent) | R$_2$ | Mixture (m) or isomer | M.p. (°C.) |
|---|---|---|---|---|
| 1 | —CH=CH—CH$_2$— | OH | m | 146–7 |
| 2 | —CH=CH—CH$_2$— | OH | trans | 202–3 |
| 3 | —CH=CH—CH$_2$— | OCH$_3$ | m | 85–6 |
| 4 | —CH=CH—CH$_2$— | NH$_2$ | trans | 191–2 |
| 5 | —CH=CH—CH$_2$— | NH$_2$ | m | 170–1 |
| 6 | —CH=CH—CH$_2$— | ONa | m | 215–6 |
| 7 | —CH=C(CH$_3$)—CH$_2$— | OC$_2$H$_5$ | cis | 96–7 |
| 8 | —CH=C(CH$_3$)—CH$_2$— | OC$_2$H$_5$ | trans | 81–2 |

The compounds of the invention were subjected to pharmacological trials which demonstrated their activity on the central nervous system.

The acute toxicity was determined in mice intraperitoneally. The LD$_{50}$ (50% lethal dose), inducing death in 50% of animals, ranges from 500 to >1000 mg/kg.

The anti-depressant activity of the compounds was demonstrated by the antagonism towards the head twitches induced by L-5-hydroxytryptophan in mice.

The mice (CD1 males, Charles River France; 18–22 g body weight) receive the products to be studied, at increasing doses, or the solvent, simultaneously with L-5-HTP subcutaneously at a dose of 250 mg/kg. Forty five minutes after this injection of 5-HTP, the number of head twitches is counted for each mouse for one minute.

For each treatment, the average number of head twitches, and also the percentage variation relative to the control batch, are calculated.

From the effect/dose curve, the AD$_{50}$ (50% active dose, or dose which reduces by 50% the average number of head twitches) is determined by the graphic method of Miller and Tainter (1944).

The AD$_{50}$ of the compounds of the invention varies from 20 to 60 mg/kg orally.

The anticonvulsant activity of the compounds was demonstrated by the antagonism towards bicuculline-induced mortality in mice.

Bicuculline is a relatively selective blocker of the post-synaptic GABA-ergic receptors, and its convulsant and lethal effects are antagonised by the compounds which raise the cerebral GABA levels or possess GABA-mimetic activity.

The 50% active dose (AD$_{50}$), the dose which protects 50% of the animals against the effect of bicuculline, was measured for the substances studied.

The AD$_{50}$ of the compounds of the invention varies from 20 to 100 mg/kg orally.

The compounds of the invention are active as antidepressants and anticonvulsants, and also possess anxiolytic, analgesic and anti-inflammatory properties. They can be used in human and veterinary therapy for the treatment of various diseases of the central nervous system, for example for the treatment of depressions, psychoses, and certain neurological diseases such as epilepsy, spasticity and dyskinesia.

The invention consequently comprises all pharmaceutical compositions containing the compounds (I) as active principles, in combination with any excipients suitable for their administration, especially orally, (tablets, dragees, gelatine capsules, capsules, pills, solutions or suspensions to be taken by mouth) or parenterally.

The daily dosage can range from 100 to 3000 mg.

We claim:

1. Diphenylazomethane derivatives of formula (I)

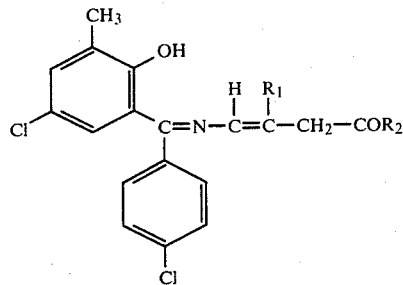

wherein $R_1$ is hydrogen or methyl and $R_2$ is an —OH, —OM (wherein M is an alkali metal or alkaline earth metal), —NH$_2$ or —O(C$_{1-4}$ alkyl) group, said derivative being in the form of cis or trans isomers or mixtures of said isomers.

2. Diphenylazomethine derivatives according to claim 1 wherein $R_2$ is —OH, —OCH$_3$, —OC$_2$H$_5$, —NH$_2$ or —ONa.

3. A pharmaceutical composition which comprises, as active ingredient, a diphenylazomethine derivative as claimed in claim 1, in association with a pharmaceutically acceptable excipient.

* * * * *